United States Patent
Callegari

(10) Patent No.: US 10,345,318 B2
(45) Date of Patent: Jul. 9, 2019

(54) METHOD FOR THE DIAGNOSTIC DETERMINATION OF THE RISK CAUSED BY AN ALTERED OXIDATIVE BALANCE

(71) Applicant: H&D S.R.L., Parma (IT)

(72) Inventor: Gabriele Callegari, Medesano (IT)

(73) Assignee: H&D S.R.L., Parma (IT)

( * ) Notice: Subject to any disclaimer, the term of this patent is extended or adjusted under 35 U.S.C. 154(b) by 0 days.

(21) Appl. No.: 15/300,357

(22) PCT Filed: Mar. 31, 2015

(86) PCT No.: PCT/IB2015/052357
§ 371 (c)(1),
(2) Date: Sep. 29, 2016

(87) PCT Pub. No.: WO2015/151023
PCT Pub. Date: Oct. 8, 2015

(65) Prior Publication Data
US 2017/0184618 A1    Jun. 29, 2017

(30) Foreign Application Priority Data
Apr. 1, 2014 (IT) .............................. MI2014A0575

(51) Int. Cl.
G01N 33/00 (2006.01)
G01N 33/92 (2006.01)
G01N 33/52 (2006.01)
G01N 33/84 (2006.01)

(52) U.S. Cl.
CPC ............ *G01N 33/92* (2013.01); *G01N 33/52* (2013.01); *G01N 33/84* (2013.01); *G01N 2800/7009* (2013.01)

(58) Field of Classification Search
CPC ..................................................... G01N 33/92
USPC ......................................................... 436/71
See application file for complete search history.

(56) References Cited

U.S. PATENT DOCUMENTS 6,569,683 B1    5/2003 Hirotomo et al.

FOREIGN PATENT DOCUMENTS

EP    0797993 A1    10/1997
JP    2003302396 A   10/2003
WO   2012/018535 A2   2/2012

OTHER PUBLICATIONS

International Search Report and Written Opinion for corresponding Application No. PCT/IB2015/052357 (Jul. 13, 2015).
Vassalle et al., "An Oxidative Stress Score as a Combined Measure of the Pro-Oxidant and Anti-Oxidant Counterparts in patients with Coronary Artery Disease," Clin. Biochem. 41:1162-1167 (2008).
Vassalle et al., "Elevated Levels of Oxidative Stress as a Prognostic Predictor of Major Adverse Cardiovascular Events in patients with Coronary Artery Disease," J. Atherosclerosis Thromb. 19(8):712-717 (2012).
Cornelli et al., "The Oxidative Stress Balance Measured in Humans with Different Markers, Following a Single Oral Antioxidants Supplementation or a Diet Poor of Antioxidants", J. Cosmetics Dermatol. Sci. Appl. 1:64-70 (2011).
Cekic et al., "Correlation of Total Antioxidant Capacity with Reactive Oxygen Species (ROS) Consumption Measured by Oxidative Conversion," J Agric Food Chem. 61(22):5260-70 (2013).
Kubo et al., "Spectrophotometric Determination of Free Radicals and Reactive Oxygen Species with N,N-dimethyl-p-phenylendiamine," Bunseki Kagaku 57:667-671 (2008).
Iga et al., "Development of New Division Quantitative Method of the Hydro Pell Oxide in the Blood Which Becomes Index of Oxidation Degree of Stress," Nenkai Pharm 29P-pm 480 (2010).

*Primary Examiner* — Christopher Adam Hixson
*Assistant Examiner* — Emily R. Berkeley
(74) *Attorney, Agent, or Firm* — Pepper Hamilton LLP

(57) ABSTRACT

A method is described for the diagnostic determination of the risk caused by an altered oxidative balance, comprising the photometric measurement of total cholesterol, hydroperoxides, and antioxidant capacity, on the basis of which the protective index, the oxidative index and the risk index caused by an altered oxidative balance (or 'OBRI') are calculated. This latter index has proved to be particularly dependable and reliable in determining the status of the oxidative balance in relation to cholesterol levels, being highly predictive of cardiovascular risk.

6 Claims, No Drawings

METHOD FOR THE DIAGNOSTIC DETERMINATION OF THE RISK CAUSED BY AN ALTERED OXIDATIVE BALANCE

This application is a national stage application under 35 U.S.C. § 371 of PCT Application No. PCT/IB32015/052357, filed Mar. 31, 2015, which claims priority of Italy Application No. MI2014A000575, filed Apr. 1, 2014, which are hereby incorporated by reference in their entirety.

FIELD OF THE INVENTION

The present invention concerns a method for the diagnostic determination of the risk caused by an altered oxidative balance, comprising the photometric measurement of total cholesterol, hydroperoxides, and antioxidant capacity, on the basis of which the protective index, the oxidative index and the risk index caused by an altered oxidative balance (or 'OBRI') are calculated. This latter index has proved to be particularly dependable and reliable in determining the status of the oxidative balance in relation to cholesterol levels, being highly predictive of cardiovascular risk.

BACKGROUND OF THE INVENTION

The evaluation of the Oxidative Stress (OS) condition assumes particular prognostic importance in the case of patients with cardiovascular diseases. When the excessive amount of biological molecules oxidised in the blood (serum or plasma) is not compensated by an adequate antioxidant capacity, OS is generated, which, if protracted over time, determines a reduction in life expectancy, particularly in patients with cardiovascular disease (Vassalle C. et al., "*Elevated levels of oxidative stress as a prognostic predictor of major adverse cardiovascular events in patients with coronary artery disease*", J Atheroscler Thromb. 2012; 19(8):712-7). In the human and animal body, the measurement of hydroperoxides (ROOH) [where R represents a molecule having a chemical nature other than simple hydrogen up to macromolecules such as lipids, glycerophospholipids, proteins, carbohydrates, DNA, RNA], is considered among the most reliable markers of OS [Cornelli U. et al., "*The Oxidative Stress Balance Measured in Humans with Different Markers, Following a Single Oral Antioxidants Supplementation or to Diet Poor of Antioxidants*", Journal of Cosmetics, Dermatological Sciences and Applications, 2011, 1, 64-70].

ROOH are the expression of almost all biological macromolecules at the initial stage of the oxidation process in that they represent the condition common to all molecules capable of propagating the OS once they come into contact with $Fe^{2+}$ (ubiquitous metal) by means of the known 'Fenton reaction':

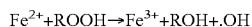

$$Fe^{2+} + ROOH \rightarrow Fe^{3+} + ROH + .OH$$

This reaction brings about the formation of a hydroxyl radical (.OH), which is by far the most powerful oxidant in the human body, being provided with a reaction half-life in the order of $10^{-9}$ seconds. Since ROOH are relatively stable, they circulate freely in both the intracellular and extracellular blood and interstitial context, with the characteristic of carrying their oxidative potential away from the point of formation. It is this very latter characteristic that makes them dangerous diffusers of OS that are far more harmful than the other, more rapidly reactive species (e.g. ROS or RNS, respectively oxygen- or nitrogen-reactive species) having local/immediate action (such as $O_2.$ or .OH, respectively superoxide and hydroxyl radical).

The hypothesis of the role of lipids and oxidised lipoproteins in determining atherosclerosis is established and in this context oxidised lipoproteins (particularly LDL) seem to be the main culprits. All lipoproteins contain cholesterol and its esters.

As for the rest of the lipids, cholesterol (Ch) is subjected to oxidation phenomena that derive from both enzymatic and non-enzymatic processes, which can be of endogenous origin or due to an ingestion of oxidised cholesterol that is generated during food storage and cooking processes.

In general, the oxidative processes of cholesterol lead to the formation of oxysterols (OxChs), at least four of which are endogenous in origin. Three of these, respectively 7α-hydroxycholesterol, 24-hydroxycholesterol, 27-hydroxycholesterol, derive from the oxidative process that takes place in the cytochromes P450 due to the formation of bile salts, while the fourth, 4β-hydroxycholesterol, is not correlated to the synthesis of these endogenous salts. An intermediate between Ch and 7β-hydroxycholesterol is represented by 7β-hydroperoxycholesterol, which is a classic hydroperoxide that can carry out the Fenton reaction and is thus capable of propagating OS.

A part of the OxChs can be deemed physiological and functional due to the polarity/mobility that allows them to cross the membranes more easily (with a speed 3 orders of magnitude higher than that of Ch, so as to represent a means of eliminating the cell excess of Ch. However, their excess is also harmful and such as to rapidly trigger the reactive cell self-destruction (apoptosis) or aggression system on the part of the macrophages, which will consequently result in removal of the cell itself.

It should lastly be noted that food cholesterol, which intake is on average in the order of a hundred or so milligrams/day, can already be in oxidised form, due to inadequate (and/or prolonged) storage of food, as well as following cooking of the food. In this form, as is moreover the case for all lipids, it is partially absorbed and incorporated into the chylomicrons that form inside the intestinal cells (enterocytes), and unique among oxidised lipids, can be transferred to all lipoproteins (the other oxidised lipids are limited to chylomicrons and remnants). OxChs are therefore used in the formation of variable-density lipoproteins (VLDL, HDL), which will already be partially oxidised and can trigger further oxidation processes by propagation (being circulating). It should be noted that, in terms of oxidation, it is important to consider total VLDL cholesterol, IDL (remnants), LDL or HDL, without distinction in that any cholesterol structure can be oxidised, as such or in esterified form.

Given the enormous importance of cholesterol, both in the structural and metabolic sense, it is equipped with a broad defence system.

The first line of defence is its esterification with fatty acids (of different carbon chain length). This process allows the deposition of cholesterol inside the lipoproteins. In normal conditions, Ch is collected both as such and in its esterified form by hepatic and intestinal ACAT A: Cholesteryl Acyl Transferase) and is then conveyed to the high-density lipoproteins (HDL). These will subsequently transfer it through transporter proteins (i.e. Cholesteryl Ester Protein Transporters or CEPT) to the other, more low-density lipoproteins (primarily to VLDL and to LDL), exchanging it with the triglycerides. The transfer of the triglycerides, which will be conveyed (by the same HDL) towards the liver with the esterified cholesterol residue, is operated in this way, both as such and as ChOx.

The second line of defence is represented by the antioxidant enzyme systems present in the HDL themselves, the paraoxonases (PON). These are assisted by the circulating antioxidant network (AO), which comprise a varied series of derivatives ranging from albumin, uric acid and the vitaminic (e.g. Vit E and Vit C) or non-vitamin (e.g. polyphenols) antioxidants taken with food.

The third line of defence is represented by the antioxidant systems of the cellular compartment, primarily represented by free glutathione (GSH) and by classic intracellular antioxidants (e.g. B-group vitamins, coenzyme Q10, lipoic acid), as well as by enzymatic antioxidants such as catalases, peroxidases, glutareductases.

Since ROOH are relatively stable, they represent an oxidative threat for both structural and metabolic cholesterol. However, the oxidative process must be seen as a ratio of the oxidative entities to the oxidisable entities. This process follows the stoichiometric rule for which the concentrations of both the molecular components involved in the oxidative and protective relationships must be evaluated.

The aim of the present invention is thus to identify a method that allows the risk caused by an altered oxidative balance to be reliably, reproducibly, repetitively and economically evaluated.

SUMMARY OF THE INVENTION

The above-indicated aim has been achieved by means of a method for the determination of this risk caused by an altered oxidative balance. This method involves the steps of:
a) providing a biological sample,
b) photometrically measuring total cholesterol $TC_\tau$ measured at time t, and optionally the basal cholesterol $TC_b$;
c) photometrically measuring hydroperoxides ROOH;
d) photometrically measuring the antioxidant capacity AC;
e) calculating the protective index PI, according to the formula: $PI=AC/TC_\tau$;
f) calculating the oxidative index OI, according to the formula: $OI=ROOH/TC_\tau$; and
g) calculating the risk index caused by an altered oxidative balance (or 'OBRI'), according to the formula [a]: $OBRI=OI \times K1/PI \times \Delta TC$,
wherein K1 is a constant equal to 9.1 in a human being and equal to 5.95 in a rat, and $\Delta TC$ is the ratio $TC_\tau/TC_b$.

The characteristics and the advantages of the present invention shall become clearer from the detailed description provided hereunder and from the Example embodiments provided by way of a non-limiting example.

DETAILED DESCRIPTION OF THE INVENTION

The object of the invention is thus a method for the diagnostic determination of the risk caused by an altered oxidative balance, said method comprising the steps of:
a) providing a biological sample;
b) photometrically measuring total cholesterol $TC_\tau$ measured at time t, and optionally the basal cholesterol $TC_b$;
c) photometrically measuring hydroperoxides ROOH;
d) photometrically measuring the antioxidant capacity AC;
e) calculating the protective index PI, according to the formula: $PI=AC/TC_\tau$;
f) calculating the oxidative index OI, according to the formula: $OI=ROOH/TC_\tau$; and
g) calculating the risk index caused by an altered oxidative balance (or 'OBRI'), according to the formula [a]: $OBRI=OI \times K1/PI \times \Delta TC$,
wherein K1 is a constant equal to 9.1 in a human being and equal to 5.95 in a rat, and $\Delta TC$ is the ratio $TC_\tau/TC_b$.

The present invention therefore concerns a diagnostic method that allows measurement of all relevant parameters for evaluation of the risk caused by an altered oxidative balance, i.e. TC, ROOH, AC, OI, PI and OBRI.

'Biological sample' means any fluid of animal origin, such as for example saliva, serum, plasma, whole blood, urine, tears, sweat. Preferably, said biological fluid is saliva, serum, plasma, or urine.

A photomer suitable for reading a $\lambda$ ranging between 380 and 780 nm, but preferably between 470 and 550 nm, can be used to implement the method of the invention.

In one, particularly preferred, embodiment, $\lambda$ is 505 nm.

Preferably, the photometer is careened and maintained by thermostating at a temperature of preferably 37° C., better if equipped with thermostat suitable for the rapid heating (<1 min) of biological samples.

In a preferred embodiment, the present invention concerns an integrated analytical system for implementing the method of the invention, comprising a photometer, a thermostatic centrifuge, a display, a printer, and an electronic processing unit capable to acquire the photometric measurements of steps b)-d) and to calculate the indices of steps e)-g) of the method of the invention.

Said integrated system thus comprises a photometer and a thermostatic centrifuge that allows the operator to have a single instrument capable of exercising both photometer and centrifuge functions. The system also has a self-instructing display that also provides operating messages (in various languages), in addition to photometer and centrifuge temperatures. This is possible thanks to the electronic processing unit that manages the instrumentation and that is able to calculate the indices of steps e)-g) of the method of the invention, having acquired the photometric measurements b)-d). Lastly, the system also integrates a printer that is able to issue a receipt with customisable header of the outcome of the measurements performed and of the calculation of the indices.

The centrifuge is suitable for containing cubic test tubes [1 cm×1 cm], preferably from 2 to 4, with content up to 5 ml. The centrifuge is thermostated in line with the photometer and preferably operates at 6000 rev/min±5%.

Measurement of Total Cholesterol (TC)

The measurement of total cholesterol, or TC, is performed photometrically.

Commercially available instrumentation for colorimetric enzyme determinations can be used for such purposes.

"Open"-system instrumentation that combine a photometer and a dry thermostating compartment in a single analytical unit, both managed by a computerised system that is able to receive, process and export data, are particularly suitable. Preferably, the photometer is arranged for at least 6 filters (340, 405, 505, 546, 578 and 630 nm), i.e. it is able to cover the spectral range between 320 and 680 nm. The thermostating system preferably covers the entire interval between 20 and 45° C. (preferably if with a sensitivity of 0.1° C. and a stabilisation time, from 25 to 37° C., of about 7 min).

Measurement of Hydroperoxides (ROOH)

The measurement of hydroperoxides, or ROOH, is also carried out photometrically and known instrumentation and methods, such as the test referred to as 'd-ROMs', as per European patent EP0783692, or the method described in a co-pending international patent application no. PCT/IB2013/059111, can be used in this case also.

The Applicant has nevertheless developed another test, briefly referred to as 'd-ROMs FAST', which is preferably used in the method of the invention for the measurement of hydroperoxides. Therefore, under another aspect, the present invention relates to a method for the determination of the oxidising power of hydroperoxides in biological samples, said method comprising the steps of:

i) providing an aqueous solution A comprising sulfuric acid and a chromophore agent of formula (I)

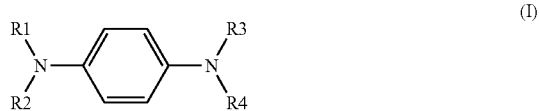

or salt thereof, where $R^1$, $R^2$, $R^3$ and $R^4$ are, independently of one another, H, $-CH_3$, $-C_2H_5$, or halide;

ii) providing an aqueous solution B comprising acetic acid, and alkali or alkaline-earth metal hydroxide;

iii) providing an aqueous solution C comprising Fe(III) salt and sulfuric acid;

iv) providing a biological sample;

v) combining the solution A, the solution B, the solution C and the biological sample and measuring the absorbance of the resulting mixture at $t_0$ and at $t_1$, wherein $t_0$ is 45 to 70 seconds and $t_1$ is 2 to 3 minutes after combining to form said mixture, and vi) subtracting the absorbance at $t_0$ from the absorbance at $t_1$, thus obtaining the value of the oxidizing power of hydroperoxides in the sample in question in terms of the concentration of $H_2O_2$ equivalents, according to Lambert-Beer's law.

The above method advantageously allows the Fenton reaction to be accelerated and stabilised, surprisingly, by means of the suitable combination of reagents as reported above. This combination allows a faster and more accurate measurement of hydroperoxides. In reacting with the Fe(III), these hydroperoxides generate radicals that in turn radicalise the chromophore. In this form, the latter assumes colour in proportion to the concentration of radicals, which can be photometrically detected at 505 nm, and allows the elimination of certain manual steps. The reagents used have surprisingly allowed test performance times to be reduced, as the reading of $t_1$ can also be carried out just 2 minutes after preparing the mixture, instead of after the at least 5 minutes needed to achieve the same result with the dROMs test, thus advantageously with a time reduction of up to 60%.

Moreover, the method of the invention resulted in a more extended linearity interval being achieved in the calculation of the oxidising power of biological samples, i.e. 50-600 U.Carr, where 1 U. Carr corresponds to 0.08 mg/dL of $H_2O_2$.

In addition, the invention advantageously allows a biological control sample solution to be used as a control "standard" sample for the quality control of the reagents.

In the d-ROMs FAST test, the biological sample analysed is preferably preliminarily centrifuged for variable times of between 30 and 90 seconds, depending on the fluid to be analysed.

One cuvette (of cubic measurement; 1 cm×1 cm with 5 mL volume capacity), referred to as "Cuvette 1", one Eppendorf and one glass phial are respectively pre-dosed with an aqueous solution A, an aqueous solution B and an aqueous solution C. The aqueous solution C and the biological sample are added to the Eppendorf containing the aqueous solution B. It is stirred and the content of the Eppendorf is poured into Cuvette 1 containing the aqueous solution A.

After stirring, the Cuvette 1 is subjected to baseline photometric measurement at $t_0$ and, after a certain time, to final photometric measurement at $t_1$.

The photometric measurements are expressed in terms of Carr.U., where 1 Carr.U. corresponds to 0.08 mg/dL of $H_2O_2$.

According to a preferred embodiment, the chromophore is provided in condensed form, where 'condensed' means that the aqueous solution in which the chromophore is dissolved is allowed to evaporate to dryness. This advantageously allows greater stability and the drastic reduction of the manual steps, on the other hand provided for by the known test.

Preferably, said chromophore agent is N,N-diethyl-p-phenylenediamine or a salt thereof.

Suitable chromophore salts are sulfate, oxalate, fumarate, chloride, phosphate, nitrate, and mixtures thereof.

Suitable Fe(III) salts are chloride, chlorate, ammonium sulfate, sulfate, sulfide, phosphate, nitrate, acetate, succinate, fumarate, gluconate, lactate, and a mixture thereof. Preferably, said Fe(III) salt is chloride.

Preferably, said alkali or alkaline-earth metal hydroxide is potassium, sodium, calcium, magnesium or a mixture thereof.

In said aqueous solutions, the solvent is water, preferably demineralised or deionised water. Preferably, said chromophore is in a concentration of 0.019 to 0.57 mol/l in the aqueous solution A, more preferably of 0.030 to 0.45 mol/l. Preferably, said chromophore is in a concentration of 0.0072 to 0.22 mol/l in the resulting mixture in step v).

Preferably, sulfuric acid is in a concentration of 0.17 to 0.93 mol/l in the aqueous solution A, more preferably of 0.20 to 0.80 mol/l.

Preferably, the acetic acid is in a concentration of 0.17 to 0.35 mol/l in the aqueous solution B, more preferably of 0.20 to 0.30 mol/l. Preferably, the acetic acid is in a concentration of 0.16 to 0.33 mol/l in the resulting mixture in step v).

Preferably, the alkali or alkaline-earth metal hydroxide is in a concentration of 0.10 to 0.35 mol/l in the aqueous solution B, more preferably of 0.15 to 0.30 mol/l. Preferably, the acetic acid is in a concentration of 0.13 to 0.33 mol/l in the resulting mixture in step v).

Preferably, the Fe(III) is in a concentration of 0.00040 to 1.0 mol/l in the aqueous solution C, more preferably of 0.001 to 0.8 mol/l. Preferably, the Fe(III) is in a concentration of 0.00033 to 0.6 mol/l in the resulting mixture in step v).

Preferably, sulfuric acid is in a concentration of 0.001 to 0.83 mol/l in the aqueous solution C, more preferably of 0.005 to 0.60 mol/l.

Preferably, sulfuric acid is in a concentration of 0.020 to 0.78 mol/l in the resulting mixture in step v).

According to one preferred embodiment, in the aqueous solution A, said chromophore is in a concentration of 0.019 to 0.57 mol/l, the sulfuric acid is in a concentration of 0.17 to 0.93 mol/l, in the aqueous solution B acetic acid is in a concentration of 0.17 to 0.35 mol/l, the alkali or alkaline-earth metal hydroxide is in a concentration of 0.10 to 0.35 mol/l, and in the aqueous solution C Fe(III) is in a concentration of 0.0004 to 1.0 mol/l, the sulfuric acid is in a concentration of 0.001 to 0.83 mol/l.

According to one particularly preferred embodiment, the aqueous solution A comprises water, N,N-diethyl-p-phenylenediamine or a salt thereof in a concentration of 0.03-0.05 mol/l, sulfuric acid in a concentration of 0.70-0.73 mol/l, the aqueous solution B comprises water, acetic acid in a concentration of 0.25-0.27 mol/l, and sodium hydroxide in a concentration of 0.15-0.20 mol/l, and the aqueous solution C comprises water, Fe(III) salt in a concentration of 0.50-0.55 mol/l, and sulfuric acid in a concentration of 0.08-0.10 mol/l.

Also preferred is the embodiment wherein the aqueous solution A comprises water, N,N-diethyl-p-phenylenediamine or a salt thereof in an amount of 0.1-3 mg, sulfuric acid in an amount of 0.1-1.4 µl, the aqueous solution B comprises water, acetic acid in an amount of 0.01-0.02 ml, and sodium hydroxide in an amount of 5-8 mg, and the aqueous solution C comprises water, Fe(III) salt in an amount of 1-8 µg, and sulfuric acid in an amount of 0.01-0.2 µl. In a particularly preferred embodiment, the composition of the three aqueous solutions is the one reported in Table A.

TABLE A

Preferred composition for evaluation of the ROOH

| | Reagents | Amount | Volume |
|---|---|---|---|
| Biological sample | | | 10 µL |
| Solution A | condensed N,N-diethyl-p-phenylenediamine | 0.2 mg | 20 µL |
| | sulfuric acid (95-98%) | 0.8 µL | |
| | Demineralised water | q.s. to volume | |
| Solution B | Acetic acid | 0.015 mL | 1000 µL |
| | NaOH | 7.5 mg | |
| | Demineralised water | q.s. to volume | |
| Solution C | Iron (III) | 5.3 µg | 10 µl |
| | Sulfuric acid (95-98%) | 0.5 µL | |
| | Demineralised water | q.s. to volume | |
| Total | | | 1040 µL |

In this particularly preferred embodiment, the Eppendorf containing the solution C in the amount of 10 µl is added to the Eppendorf containing the solution B of Table A, and after stirring for 10 seconds, the biological sample in the amount of 10 µL is added, and after stirring for 10 seconds, the content of the Eppendorf is poured into the Cuvette 1, containing the solution A. After 150 seconds, the Cuvette 1 is subjected to photometric measurement. The measurement is provided in terms of Carr.U. where 1 Carr.U corresponds to 0.08 mg/dL of $H_2O_2$. In another aspect, the present invention concerns a kit for implementing the above method, comprising
 a) at least one container comprising a chromophore agent of formula (I)

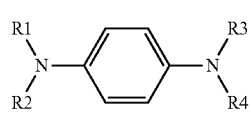

or salt thereof, where $R^1$, $R^2$, $R^3$ and $R^4$ are, independently of one another, H, —$CH_3$, —$C_2H_5$, or halide;

b) at least one container comprising the acetate buffer;
 c) at least one container comprising Fe(III) salt; and
 d) a leaflet comprising instructions for performing the determination of the oxidising power of hyperperoxides.

Preferably, said chromophore is present in the container a) of the kit in condensed form.

It is to be understood that all the aspects identified as preferred and advantageous for the measurement of hydroperoxides, are also to deemed analogously preferred and advantageous for the kit for the implementation thereof.

Measurement of Antioxidant Capacity (AC)

Measurement of the antioxidant capacity AC is performed photometrically and, in this case also, known instrumentation and methods can be used, such as for example the test referred to as BAP (biological antioxidant potential) test, which evaluates the antioxidant power of the biological sample, preferably serum plasma, in terms of the latter's ability to reduce ferric ions to ferrous ions, photometrically detecting the colour variations of a specific chromogen. In the BAP test, the biological sample is mixed with a Reagent 1 comprising an alcoholic solution of thiocyanate, and a Reagent 2 comprising a ferric salt. In the BAP test, therefore, the sample to be analysed is dissolved in a coloured solution obtained by adding a source of ferric ions, preferably $FeCl_3$, to the thiocyanate solution. After a short incubation (5 minutes), the solution discolours and the discolouration will be more marked the more the components of the sample tested have been able to reduce, in the interval considered, the ferric ions initially present, which are responsible for the formation of the colour complex. By photometrically evaluating the extent of this discolouration, it is possible to determine the amount of ferric ions reduced and, ultimately, the reducing capacity, i.e. the antioxidant power of the sample tested, compared to a reference sample, known as a calibrator.

Alternatively, the measurement of antioxidant capacity is carried out according to the method described in international patent application WO 2011/104267 and abbreviated for convenience to 'PAT' test.

According to this PAT test, a cuvette (of cubic measurement; 1 cm×1 cm with 5 mL volume capacity), referred to as "Cuvette 2", is used.

The Cuvette 2 is pre-dosed with a Reagent 1 and with a Reagent 2.

Reagent 1 comprises alcoholic solution of thiocyanate, while Reagent 2 comprises an inorganic zirconium salt and a ferric salt.

Preferably, said alcoholic solution is a water-alcohol mixture.

Preferably, said inorganic zirconium salt is selected from the group consisting of fluoride, chloride, bromide, iodide, carbonate, sulfate, nitrate and mixtures thereof. More preferably, it is selected from the group consisting of fluoride, chloride, bromide, iodide, and mixtures thereof. In a preferred embodiment, said inorganic zirconium salt is $ZrCl_4$.

Preferably, said ferric salt is selected from the group consisting of fluoride, chloride, bromide, iodide, carbonate, sulfate, nitrate, and mixtures thereof. In a preferred embodiment, said ferric salt is nitrate.

The Cuvette 2 is subjected to baseline photometric measurement, and after a given time (t), to final photometric measurement.

Preferably, said time (t) is 40-120 seconds after the baseline photometric measurement, more preferably 50-100 seconds after the baseline photometric measurement.

The photometric measurements are expressed in terms of U Cor (where 1 U Cor corresponds to 1.4 µmol/L of Vit C).

In a particularly preferred embodiment, the composition of Reagents 1 and 2 is the one reported in Table B.

TABLE B

Preferred composition for evaluation of the AC by means of PAT test

| Reagents | | Amount | Volume |
|---|---|---|---|
| Biological sample | | | 10 µl |
| Reagent 1 | isopropyl alcohol | | 600 µl |
| | Demineralised $H_2O$ | | 350 µl |
| | KSCN | 0.11 mmol | 10 µl |
| Reagent 2 | $ZrCl_4$ | 47.2 mmol | 5 µl |
| | $Fe(NO_3)_3$ | 5.01 mmol | |
| | | | 35 µl |
| Total | | | 1010 µl |

40 µL of the Reagent 2 of Table B are added to Cuvette 2 and, after 10 seconds of stirring, it is placed into the photometer for baseline reading. Immediately thereafter, the first photometric reading for the antioxidant capacity of PAT is performed. 10 µL of biological sample are immediately added to Cuvette 2, stirred for 10 seconds and Cuvette 2 is re-inserted into the photometer.

60 seconds after the first reading, the instrument performs the second reading of the sample, which will be expressed in U Cor (where 1 U Cor corresponds to 1.4 µmol/L of Vit C).

In a preferred embodiment, the respective values of ROOH and antioxidant capacity AC via PAT can be provided by means of a thermal printer incorporated into the bottom of the photometer of the system of the invention.

Calculation of the Risk Caused by Altered Oxidative Balance (OBRI, Oxidative Balance Risk Index)

Determination in a human being takes place as follows, starting from the formula [a]:

$$OBRI = OI \times K1 / PI \times \Delta TC \quad [a]$$

$K_1$ is the necessary factor for obtaining the value of OBRI=1 (i.e. risk 1) when the respective levels of TC, ROOH and antioxidant capacity are represented by average normal levels that correspond to: $TC_b$=200 mg/dL; d-ROOH=275 Carr.U.; AC=2500 U Cor.

$TC_\tau$, on the other hand, is the cholesterol value at the time of determination.

For the values reported for the average normal levels, the calculation of OBRI will be =1 only in the case in which $K_1$ is =9.1

In fact, again in the condition of average normal levels, the corresponding values of OI and PI are as follows:

OI=1.375 [i.e. 275/200]; PI=12.5 [i.e. 2500/200]

Therefore OBRI will be 1.375×9.1/12.5, or =1 (unitary risk)

For the calculation of OBRI in the condition of a cholesterol level in the correspondence of a time t, i.e. $TC_\tau$ (i.e. the value of the cholesterol of the subject in question at the time of the determination), replacing in the [a] formula the value of K1 and the value of $TC_b$, the value of the OBRI will be determined by:

$$OBRI = OI \times 9.1 / PI \times (TC_\tau/200)$$

which, simplified, becomes:

$$OBRI = OI/PI \times 0.0455 \times TC_\tau \quad [b]$$

[b] is therefore the simplified formula to apply in relation to the current levels of ROOH, AC and $TC_\tau$ in a human being.

In a rat, on the other hand, K1=5.95.

This differentiation between human and rat depends on the fact that the normal cholesterol values in a rat are not known. These in fact depend on the strain, on the diet used, on the age of the animal. The baseline cholesterol value (i.e. $TC_b$ at the time of the first sample was taken) and the value at the time that is to be considered (i.e. $TC_\tau$) are therefore used as reference. This is why in step b) of the method, the $TC_b$ measurement is indicated as optional, i.e. in humans a $TC_b$ value=200 mg/dL is assumed, while in the rat, the $TC_b$ must be measured.

From analysis of the frequency distributions reported in Example 1, performed on 146 animals, it has been possible to highlight that if a median value of OBRI=1 (as unitary risk value) is to be obtained, the K1=5.95 factor must be used.

As will be seen in detail in the following Examples that follow, an interesting correlation between the OBRI index reduction and the CIMT improvement has emerged, where CIMT stands for Carotid Intima-Media Thickness, i.e. the measurement of the arterial segment of the carotid artery used as cardiovascular risk marker.

Cardiovascular diseases, such as atherosclerosis, can progress silently for many years, later determining clinical events affecting the cardiovascular system that could prove even fatal, such as heart attack and stroke. The possibility of identifying early vascular alterations capable of predicting the development of these diseases, and thus of reducing fatal events, is essential in developing a dedicated diagnostic method, which must certainly offer high reliability but also speed of execution.

In this sense, it was found that the method of the invention allows these needs to be met. OBRI, in particular, has proved to be an extremely reliable index in determining real improvement of the oxidative balance in relation to cholesterol levels, such as that only in subjects in whom the index significantly improves (>0.8) can a regression of the atherosclerotic vascular disease be observed, as shown in Example 4.

It is to be understood that, for the purposes of the method of the invention, all possible combinations of the preferred aspects of the measures in the individual steps of the method itself, as reported above, are analogously preferred, and therefore described.

Example embodiments of the present invention are provided below by way of a non-limiting example.

EXAMPLES

Example 1

Evaluation of the OI, PI and OBRI Indices in Rats Maintained on a Standard Diet 146 male rats of the Wistar-Charles River strain, weighing between 180 and 240 g, were analysed. The animals were allocated in individual cages and fed with a standard diet (#48 Randoin-Causeret).

After housing over a 7-days period in controlled conditions (25° C. and ambient humidity of 60%, food and water ad libitum), in the morning (8th day) the animals were subjected to blood sample taking from the caudal vein, in the amount of not more than 0.25 mL, by means of a heparinised syringe. The sample was centrifuged for isolation of the plasma, which was maintained at −80° C. until the time of the analysis. The animals were not fasted for sample taking.

During the first baseline determination, each animal was housed in an individual metabolic cage for urine collection at 24 h. In these conditions, the animal was fasted to prevent food contamination in the urine.

The overall experience was conducted on groups of 24-26 animals per session, for a total of six successive sessions, which took place over the space of a year and which therefore took all the seasons into account.

The following controls were performed on the samples: total cholesterol (TC) using an enzymatic colorimetric method, levels of hydroperoxides (ROOH) using the d-ROMs FAST test (with the composition of Table A) in terms of U.Carr. (where 1 U. Carr. corresponds to 0.08 mg/dL $H_2O_2$), as well as the levels of antioxidant capacity in plasma and UAT in the urine, respectively through PAT test (with the composition of Table B) in terms of U Cor (where 1 U Cor corresponds to 1.4 μmol/L Vit C) and UAT test (UAT or Urinary Antioxidant Test) in terms of μmol/L Vit C. In the determination of UAT, ROOH measurements was not performed.

The product of the urinary concentration by the urinary volume was also calculated, to evaluate if the body were operating a contraction of the excretion of antioxidants as a function of their use for controlling systematic oxidation.

For these latter d-ROMs FAST, PAT, UAT recordings, the method of the invention was used, which also provides the 01, PI and OBRI indices.

The formula [a] was used to calculate the value of OBRI: OBRI=OI×K1/PI×ΔTC where K1=of 5.95 and $\Delta TC = TC_\tau / TC_b$. This value allows the median=1, which represents the unit risk at the baseline time, to be quoted on the values recorded, The ΔTC parameter was represented by the $TC_\tau$ (current) to $TC_b$ (baseline) ratio. Therefore, in the baseline evaluation of the $TC_\tau/TC_b$ ratio, it was =1 while in subsequent ones it was the point value of $TC_\tau/TC_b$ (usually, but not necessarily≠1)

Of all the data recorded, the average and standard deviations (SD), the medians, the distribution parameters of the values obtained for the 9 variables examined, were calculated.

The results in terms of average and median values are collected in Table 1, while the distribution values, based on quintiles (from Q1 to Q5) are reported in Table 2.

TABLE 1

Average values ± SD and medians of the variables, normal range Data recorded on male rats weighing between 180 and 250 g

| Variable | Measurement | Number of cases | Average ± SD | Median |
|---|---|---|---|---|
| TC | mg/dL | 146 | 93 ± 15.2 | 94 |
| d-ROMs FAST | U. Carr. | 146 | 302 ± 82.4 | 235 |
| PAT | U Cor | 146 | 1654 ± 249.9 | 1638 |
| OI | U. Carr./mg/dL | 146 | 3.3 ± 1.13 | 3.1 |
| PI | U Cor/mg/dL | 146 | 18.1 ± 3.48 | 17.7 |
| OBRI | OI/PI × 5.95 | 146 | 1.13 ± 0.45 | 1.00 |
| PAT/d-ROMs FAST | U Cor/U. Carr. | 146 | 5.8 ± 1.81 | 5.8 |
| Urine 24 h | mL | 146 | 11.4 ± 4.13 | 11.0 |
| UAT | μmol/L Vit C | 146 | 156 ± 44.2 | 150 |

The subsequent division into quintiles allowed 5 different measurements to be configured with which it is possible to trace both the normal levels and those respectively above and below normal.

TABLE 2

Reference measurements of the variables analysed on the basis of quintiles

| | Values on the basis of quintiles | | | | |
|---|---|---|---|---|---|
| Variable | Values Very low Q1 | Values Medium-low Q2 | Values Medium Q3 | Values Medium-high Q4 | Values Very high Q5 |
| TC | <79 | 79-92 | 93-105 | 106-119 | >119 |
| d-ROMs FAST | <189 | 189-277 | 278-365 | 366-454 | >454 |
| PAT | <1313 | 1313-1556 | 1557-1798 | 1799-2041 | >2041 |
| OI | <2.3 | 2.3-3.6 | 3.7-5.0 | 5.1-6.3 | >6.3 |
| PI | <14.6 | 14.6-18.8 | 18.9-23.0 | 23.1-27.1 | >27.1 |
| OBRI | <0.82 | 0.82-1.35 | 1.36-1.88 | 1.89-2.41 | >2.41 |
| PAT/d-ROMs FAST | <3.6 | 3.7-5.2 | 5.3-6.8 | 6.9-8.4 | >8.4 |
| Urine 24 h | <9.4 | 9.5-14.8 | 14.9-20.2 | 20.3-25.6 | >25.6 |
| UAT | <112 | 112-172 | 173-231 | 232-291 | >291 |

The correlations ("r") between the variables were also evaluated. These are reported in Table 3. The p<0.01 level was used to determine the significance of the correlations. The sample size is such as to also allow the "r" values corresponding to 0.216 to be deemed significant. In general, all the correlations observed proved consistent thus also providing surely interesting indications. As concerns the TC, when its levels rise on a par with the values of the d-ROMs FAST and PAT values, the OI and IP indices also obviously reduce (as the value of TC is at the denominator), but the OBRI index does not change, attesting to the formation of a balance with protective function.

In relation to the d-ROMs FAST, it is noted that its value is directly correlated with OI and OBRI while it is inversely correlated with PAT and PI, and, obviously, with PAT/d-ROMs FAST.

The high correlation of the PAT/d-ROMs FAST index with OBRI (r=0.934, p<0.01) would seem to indicate that both of these indices represent a variable sufficient to determine the risk. However, in the examples below, it will be noted that that the PAT/d-ROMs FAST index is far less discriminating than OBRI.

As expected, PAT is directly correlated with IP and PAT/d-ROMs FAST (respectively r=0.527 and 0.722; both p<0.01) and inversely correlated with OI (r=−0.543; p<0.01) and OBRI (r=−0.729; p<0.01). These are also expected correlations as they are related to the components of the equations.

TABLE 3

Correlations between the variables: "r" values

|  | TC | d-ROMs FAST | PAT | OI | IP | OBRI | PAT/d-ROMs FAST | Vol | UAT |
|---|---|---|---|---|---|---|---|---|---|
| TC | 1 | | | | | | | | |
| d-ROMs FAST | −0.063 | 1 | | | | | | | |
| PAT | 0.284$^a$ | −0.494$^a$ | 1 | | | | | | |
| OI | −0.537$^a$ | 0.860$^a$ | −0.543$^a$ | 1 | | | | | |
| IP | −0.622$^a$ | −0.328$^a$ | 0.527$^a$ | 0.037 | 1 | | | | |
| OBRI | −0.150 | 0.934$^a$ | −0.729$^a$ | 0.848$^a$ | 0.454$^a$ | 1 | | | |
| PAT/d-ROMs FAST | −0.152 | −0.809$^a$ | 0.722$^a$ | −0.730$^a$ | 0.420$^a$ | −0.826$^a$ | 1 | | |
| Urine 24 h | −0.048 | 0.104 | −0.244$^a$ | 0.085 | −0.140 | 0.182 | −0.158 | 1 | |
| UAT | 0.010 | 0.131 | −0.062 | 0.095 | −0.026 | 0.095 | −0.154 | 0.363$^a$ | 1 |

$^a$p < 0.01

The OI index has respectively positive correlations with OBRI (r=0.848; p<0.01) and negative correlations with PAT/d-ROMs FAST (r=−0.730; p<0.01). The same can be said of PI.

As can be noted below, changes in cholesterol, which will be included in the determination of OBRI in terms of the $TC_\tau/TC_b$ ratio (i.e. $\Delta TC$), are very important for the purposes of OBRI. For this reason, it will be observed how OBRI is differentiated from the PAT/d-ROMs FAST ratio in prognostic terms. Without considering the changes in TC, OBRI would be similar to PAT/d-ROMs FAST multiplied by 5.95.

If, on the other hand, $TC_\tau$ levels are considered, the OBRI index will substantially differ from the PAT/d-ROMs FAST ratio by a factor≠ of 5.95.

This is in line with the clinical evidence that reducing cholesterol levels is to be deemed an important factor for reducing cardiovascular risk, but the oxidative balance must also be considered.

Example 2

Stability of OBRI Values in Rats

The aim of the present experience was to evaluate changes in complete oxidative balance values in a rat maintained in normal conditions.

21 rats from the group of 146 animals reported in Example 1 were analysed, which were followed for a 2-week period in the same conditions reported in Example 1, while repeating the tests in the same way.

The following indices were calculated on the variables: OI (oxidative index, i.e. d-ROMs FAST/TC); PI (cholesterol oxidation protective index, i.e. PAT/TC), PAT/d-ROMs FAST index (i.e. general oxidative balance without taking cholesterol levels into account); OBRI, in this case taking the $TC_\tau$ value (i.e. cholesterol levels after 2 weeks) and baseline values i.e. $TC_b$ into account. The results are reported in Table 4.

TABLE 4

Baseline oxidative index values and values after 2 weeks of housing in normal conditions. Average values ± SD

| Variables | Measurement | No. of animals | Baseline [$TC_b$] | After 2 weeks [$TC_\tau$] |
|---|---|---|---|---|
| TC | mg/dL | 21 | 97 ± 18.5 | 77 ± 13.6$^a$ |
| d-ROMs FAST | U. Carr. | 21 | 319 ± 83.2 | 350 ± 97.2 |
| PAT | U Cor | 21 | 1638 ± 234.4 | 1617 ± 222.2 |
| OI | U. Carr./mg/dL | 21 | 3.4 ± 1.15 | 4.7 ± 1.46$^a$ |
| PI | U Cor/mg/dL | 21 | 17.3 ± 3.43 | 21.6 ± 4.56$^a$ |
| OBRI | OI × K1/PI × $\Delta TC^b$ | 21 | 1.2 ± 0.38 | 1.1 ± 0.41 |
| PAT/d-ROMs FAST | U Cor/U. Carr. | 21 | 5.5 ± 1.73 | 5.1 ± 1.80 |
| Urine 24 h | mL | 21 | 12.3 ± 4.92 | 15.5 ± 6.92$^a$ |
| UAT | μmol/L Vit C | 21 | 162 ± 46.0 | 153 ± 66.3 |

$^a$Test t for interdependent data p > 0.01;
$^b$K1 = 5.95 and $\Delta TC = TC_\tau/TC_b$ Experience shows that in animals the TC is significantly reduced. This is a data that calls for a stabilisation of the metabolism of the animals that were subjected to a different diet from that used by the farm of the producer (Charles River) and probably the current diet (#48 Randoin-Causeret) modifies the plasma concentrations thereof.

This reduction consequently causes a reduction in the denominator (both OI and PI have the TC as common denominator) and therefore both indices tend to increase. Nevertheless, the increase of both indices does not allow a modification of the OBRI index, which remains stable. The increase in urinary excretion (p<0.01) as an expected data should in particular be noted, as in the 2-week period the weight of the animals increased on average by about 80 g, with consequent repercussion on urinary volume. The UAT value remains constant and is in line with the increase of d-ROMs FAST, indicating that body growth (see aging) affects the oxidative state, by increasing it. This phenomenon is more evident in Example 3 where the animals were followed for a time period of 28 months.

Example 3

The OBRI Index as Predictor of Survival in a Rat

The aim of this research was to determine survival in normal rats maintained in standard conditions. 21 rats belonging to the group of 146 animals reported in Example 1 were analysed.

These are the same animals reported in Example 2, which were followed for a time period of 24 months and maintained under the same standard conditions (i.e. those of Example 1).

The animals remained in the housing conditions indicated, with food and water ad libitum and were followed for a period of 28 months to check spontaneous mortality. All variables were checked after the first seven days of housing and subsequently also after 24 months of housing. Total cholesterol level checks (TC) were performed on the samples using an enzymatic colorimetric method, of the levels of hydroperoxides (ROOH) using the d-ROMs FAST test in terms of U.Carr. (where 1 U.CARR. corresponds to 0.08 mg/dL $H_2O_2$), as well as of the levels of total antioxidant reserve through PAT testing in terms of Cor U (where 1 U Cor corresponds to 1.4 mol/L Vit C).

The qualitative total of excreted antioxidants (UAT o Urinary Antioxidant Test; concentration×volume) was calculated on the urine collected on the basis of the product of the concentration and the urinary volume.

The mortality of the animals was recorded after 28 months of housing.

For two animals, death occurred prematurely with respect to normal life expectancy, one at 6 months and one at 9 months of life respectively (due to pneumonia).

The results are reported in Table 5.

Significant increases in TC ($p<0.05$) and the d-ROMs FAST test were observed, while PAT remained substantially constant. The OI index also remained constant, while the PI index and the PAT/d-ROMs FAST ratio suffered a significant reduction ($p<0.05$).

This behaviour indicated that, with the increasing age of the animals, there was the tendency to lose the oxidative balance, as evidenced by the increase of ROOH not compensated an equal increase of the PAT.

Urinary excretion increased significantly ($p<0.01$), whereas the excretion of antioxidants (UAT) remained constant in time.

Oxidative imbalance was observed in both the reduction of the PAT/d-ROMs FAST ratio (−19%; $p<0.05$) and in the increase in the OBRI (+53%, $p<0.05$). The significant different extent of modification of the two terms indicates a greater sensitivity of the OBRI index with respect to the PAT/d-ROMs FAST index.

TABLE 5

TC values and oxidative balance at baseline and after 24 months: average values ± SD

| Variables | Measurement | No. of animals | Baseline [$TC_b$] | After 24 months [$TC_t$] |
|---|---|---|---|---|
| TC | mg/dL | 19 | 98 ± 19.4 | 113 ± 19.5[a] |
| d-ROMs FAST | U. Carr. | 19 | 297 ± 53.6 | 366 ± 75.2[a] |
| PAT | U Cor | 19 | 1662 ± 233.0 | 1631 ± 365.3 |
| OI | U. Carr./mg/dL | 19 | 3.2 ± 0.99 | 3.4 ± 1.04 |
| PI | U Cor/mg/dL | 19 | 17.5 ± 3.43 | 14.9 ± 3.79[a] |
| OBRI | OI × K1/PI × $\Delta TC$[b] | 19 | 0.96 ± 0.26 | 1.47 ± 0.60[a] |
| PAT/ d-ROMs FAST | U Cor/U. Carr. | 19 | 5.8 ± 1.53 | 4.7 ± 1.87[a] |
| Urine 24 h | mL | 19 | 11.4 ± 4.15 | 18.4 ± 5.96[a] |
| UAT | μmol/L Vit C | 19 | 156 ± 58.1 | 161 ± 34.9 |

[a]Test t for interdependent data p < 0.05;
[b]K1 = 5.95 e $\Delta TC = TCt/TC_b$ This difference in sensitivity is clearly highlighted when the mortality of the animals in relation to the indices themselves is taken into consideration, as reported in Table 6.

In the 28 months, 10 deaths were observed over a total of 19 animals.

Table 6 indicates that at 28 months, 10/14 animals, in which the OBRI increased, died, while in the 5 animals, where the OBRI reduced, none died.

This difference is significant at the exact chi-square test according to Fisher (p=0.0108).

The main plasma variables, taken both individually −TC, d-ROMs FAST, PAT− and as indices, −PAT/d-ROMs FAST, OI and PI, were analysed and correlated to mortality. PAT, IP, PAT/d-ROMs FAST increases were deemed "favourable" values, while increases in TC, OI, d-ROMs FAST were deemed "unfavourable".

There is no significant difference in mortality in relation to all the other variables analysed which were quoted on exact probability values between p 0.1372 and p 0.8724, i.e. not significant. From all of this it is clear that the OBRI index has a predictive survival value while all the other variables or indices do not possess this characteristic.

TABLE 6

Relationship between indices and mortality after 28 months

| Index | | Deceased | Surviving | Totals | Fisher test |
|---|---|---|---|---|---|
| OBRI | favourable | 0 | 5 | 5 | |
| | unfavourable | 10 | 4 | 14 | |
| | Totals | 10 | 9 | 19 | p = 0.0108 |
| PAT/ d-ROMs FAST | favourable | 4 | 5 | 9 | |
| | unfavourable | 6 | 4 | 10 | |
| | Totals | 10 | 9 | 19 | p = 0.4141 |
| OI | favourable | 4 | 5 | 9 | |
| | unfavourable | 6 | 4 | 10 | p = 0.8724 |
| | totals | 10 | 9 | 19 | |
| PI | favourable | 2 | 4 | 6 | |
| | unfavourable | 8 | 5 | 13 | |
| | Totals | 10 | 9 | 19 | p = 0.2585 |
| TC | favourable | 2 | 4 | 6 | |
| | unfavourable | 8 | 5 | 13 | |
| | Totals | 10 | 9 | 19 | p = 0.2585 |
| d-ROMs FAST | favourable | 0 | 3 | 3 | |
| | unfavourable | 10 | 6 | 16 | |
| | totals | 10 | 9 | 19 | p = 0.1372 |
| PAT | favourable | 4 | 5 | 9 | |
| | unfavourable | 6 | 4 | 10 | p = 0.8724 |
| | totals | 10 | 9 | 19 | |

Example 4

OBRI Values in Relation to Improvement of Carotid Artery Thickness in Humans Suffering from Atherosclerosis 22 subjects suffering from atherosclerosis of the carotid artery, documented by ultrasound, were taken into consideration. The subjects were all male, aged between 54 and 64.

The admission criteria provided for the presence of hypercholesterolemia [230 mg/dL<TC<300 mg/dL] with triglycerides<300 mg/dL, to be subjected to statin therapy.

The exclusion criteria consisted of any other therapy or any chronic disease, therefore the subject could only be treated only with the statin. In the period of experimental analysis recurrent therapies for possible infectious diseases were permitted. This was granted providing that the episode took place at least 15 days from the experimental controls and was free from any sequela of the disease having taken place.

Both working and retired subjects and smokers and non-smokers were indiscriminately admitted.

The entire experience took place in the period of time between the start of the month of July and the second week of October 2013. The experimental controls were carried out in 2 periods: baseline or within a week before the start of treatment and after 3 months (±3 days) of treatment with a statin (limited to lovastatin or pravastatin). Statins were always used at a fixed dose of 10 mg of lovastatin and 20 mg of pravastatin respectively, always and exclusively administered before the evening meal, between 19:30 and 20:30 hours. The experience was of the "registry" type. However, the ultrasound operator and the biostatistician were both unaware of the treatments. Pravastatin was one of those commercially available (original or generic), while lovastatin was exclusively derived from the commercial product Antilip®. This product contained tablets formulated with lovastatin derived from extract of Monascus purpureus, polyglucosamine and phytosterols from Brassica campestris (respectively 5 mg, 182 mg and 150 mg).

For pravastatin, administration consisted of a single tablet, while for Antilip® administration was, in any case, of 2 tablets at the same time.

For each control, a bilateral carotid artery ultrasound was performed with PREIUS Elastosonographer Hitachi ecograph. The carotid arteries were analysed on transversal and longitudinal images. The examination included evaluation of the common carotid artery within 1.5 cm of the origin of the bulb, the bulb itself, the external and internal carotid arteries. Carotid intima-media thickness (CIMT) was measured on the images performing 5 measurements on each artery. Arterial plaques were excluded (considering as a plaque any protrusion of at least 1.5 mm inside the artery). The CIMT measurement was expressed in mm. The laboratory variables were evaluated within 3 days of the ultrasound examination and were part of the normal analytical routine for this type of patient. The evaluation consisted of: cholesterol and triglyceride levels (TC, HDL, LDL, TG); oxidative balance represented by d-ROMs FAST and by PAT with respective OI, PI and OBRI indices.

The general characteristics of the subjects are reported in Table 7.

TABLE 7

General characteristics of 22 male subjects treated with statins and ultrasound analysis: average values ± SD

| Variables | Measurement | Values |
|---|---|---|
| Age | years | 59 ± 3.2 |
| Weight | Kg | 77 ± 5.5 |
| Height | cm | 174 ± 4.0 |
| BMI | Kg/m$^2$ | 25.1 ± 1.48 |
| Profession | Yes | 18 |
| Pensioners | Yes | 4 |
| Lovastatin | mg | 10 |
| Pravastatin | mg | 20 |
| Smoke | Yes/No | 12/10 |

In order to analyse the ratio of the oxidative condition to any change in the CIMT, the correlation coefficient "r" was analysed. The results obtained are recorded in Table 8:

TABLE 8

Variables relating to the lipid, oxidative and CIMT ultrasound measurement. Average values ± SD

| Variables | Measurement | Baseline | After 12 wks | % decr. | Test t$^a$ |
|---|---|---|---|---|---|
| TC | mg/dL | 251 ± 9.3 | 198 ± 16.7 | 21 ± 7.0 | p < 0.01 |
| LDL | mg/dL | 171 ± 11.3 | 123 ± 18.6 | 28 ± 10.5 | p < 0.01 |
| HDL | mg/dL | 40 ± 3.2 | 40 ± 3.1 | | Ns |
| Triglycerides | mg/dL | 198 ± 34.9 | 176 ± 25.3 | 12 ± 9.8 | p < 0.01 |
| d-ROMs FAST | U. Carr. | 383 ± 27.5 | 330 ± 73.2 | | p < 0.01 |
| PAT | U Cor | 2173 ± 174.2 | 2592 ± 124.7 | | p < 0.01 |
| PAT/d-ROMs FAST | U Cor/U. Carr. | 5.7 ± 0.47 | 6.8 ± 0.41 | | p < 0.01 |
| OI | U. Carr./TC mg/dL | 1.5 ± 0.13 | 1.7 ± 0.41 | | Ns |
| PI | U Cor/TC mg/dL | 8.7 ± 0.71 | 13.2 ± 2.02 | | p < 0.01 |
| OBRI | OI × K1/PI$^b$ | 2.0 ± 0.16 | 1.1 ± 0.26 | 43 ± 13.8 | p < 0.01 |
| CITM | mm | 1.6 ± 0.05 | 1.5 ± 0.12 | 5 ± 7.4 | p < 0.01 |
| Correlation | r | Between CIMT (mm) reduction and OBRI index reduction = 0.546; p < 0.05. | | | |

It was noted that, with the exclusion of HDL and OI, all data recorded following treatment with statins differed significantly in a favourable sense.

Among the classic reference variables for the action of statins, it can be observed that following treatment, the TC, LDL and TG were respectively reduced by 21±7.0, 28±10.5, 12±9.8%, while for OBRI, the reduction was much significant, being 43±13.8%. It has not been possible to highlight differences between the two statins used on account of the limited number of cases for each product.

Correlation coefficients between the blood variables and their respective indices with the reduction of CIMT are collected in Table 9. The average±SD values of the variables/indices for patients in whom a reduction in CIMT>10% [10 cases] was recorded and for patients where the CIMT did not change [12 cases] are also reported.

TABLE 9

Correlation coefficients between variables/ blood indices and CIMT reduction

| Variables | "r" vs CIMT[a] | Average values ± DS | | Test t[b] |
|---|---|---|---|---|
| | | Cases with CIMT reduction >10% [10 cases] | Cases without CIMT reduction [12 cases] | |
| TC | 0.146 | 56 ± 27.8 | 50 ± 8.3 | Ns |
| LDL | 0.098 | 51 ± 29.1 | 45 ± 8.4 | Ns |
| HDL | −0.018 | 1 ± 1.3 | 1 ± 1.2 | Ns |
| TG | 0.226 | 24 ± 21.4 | 20 ± 18.0 | Ns |
| d-ROMs FAST | −0.391 | −81 ± 88.5 | −29 ± 44.1 | Ns |
| PAT | 0.370 | 462 ± 88.4 | 408 ± 220.3 | Ns |
| PAT/ d-ROMs FAST | 0.366 | 1.2 ± 0.25 | 1.1 ± 0.61 | Ns |
| OI | −0.328 | 0.0 ± 0.49 | −0.2 ± 0.25 | Ns |
| PI | 0.290 | 5.1 ± 2.7 | 4.2 ± 0.87 | Ns |
| OBRI | 0.546[a] | 1.0 ± 0.33 | 0.8 ± 0.21 | <0.05 |

[a] $p < 0.05$;
[b] test t for independent data

What emerges of interest is the correlation between the OBRI index reduction and the CIMT improvement (r=0.546; p<0.05), while all the other variables are not correlated. In confirmation of this figure, the only significant differences of the study variables are observed in those cases for which OBRI values were significantly reduced.

It should be noted that these results confirm those obtained in Example 3, in which it emerges that OBRI is the only one of the laboratory indices to be correlated with the duration of rat's life.

In conclusion, it has emerged that OBRI proves extremely reliable in determining real improvement of the oxidative balance in relation to cholesterol levels, such that only in subjects in whom the index significantly improves can a regression of the vascular atherosclerotic disease also be observed.

It indicatively emerges that, limited to the 12-week observation period, the reduction of CIMT is almost exclusively observed when the OBRI index improves by at least 45%.

The invention claimed is:

1. A method comprising the steps of:
   a) providing a biological sample;
   b) contacting a first portion of the biological sample with one or more enzymatic reagents suitable for detecting cholesterol, and detecting, photometrically, total cholesterol (TC) (mg/dL) in said biological sample as a result of said contacting;
   c) contacting a second portion of the biological sample with one or more reagents suitable for detecting hydroperoxides (ROOH), and detecting, photometrically, ROOH levels (CARR. Units) in said biological sample as a result of said contacting said second portion, wherein said one or more reagents suitable for detecting ROOH comprise:
      i) an aqueous solution A comprising sulfuric acid and a chromophore agent of formula (I)

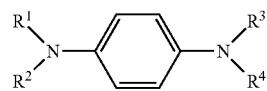

(I)

or salt thereof, where $R^1$, $R^2$, $R^3$ and $R^4$ are independently selected from the group consisting of H, —$CH_3$, —$C_2H_5$, and halide;
      ii) an aqueous solution B comprising acetic acid, and alkali or alkaline-earth metal hydroxide; and
      iii) an aqueous solution C comprising Fe(III) salt and sulfuric acid;
      wherein said second portion of the biological sample is contacted with aqueous solution A, aqueous solution B, aqueous solution C to form a mixture, and absorbance of the mixture is detected after said contacting;
   d) contacting a third portion of the biological sample with one or more reagents suitable to detect antioxidant capacity (AC), and detecting, photometrically, AC (U. Cor.) in said biological sample as a result of said contacting said third portion,
      wherein said one or more reagents suitable for detecting AC in the biological sample comprise:
      (i) a Reagent 1 comprising an alcoholic solution of thiocyanate, and a Reagent 2 comprising a ferric salt, wherein said contacting Reagent 1 and Reagent 2 with said third portion of said biological sample creates a reaction mixture, and said AC is detected in said reaction mixture as a result of said contacting;
   e) calculating the protective index (PI), according to the formula: PI=AC/TC;
   f) calculating the oxidative index (OI), according to the formula: OI=ROOH/TC; and
   g) determining oxidative balance (or 'OBRI'), according to formula [b]: OBRI=OI×K1/PI×TC,
      wherein K1 is a constant equal to 9.1 in a human being and equal to 5.95 in a rat.

2. The method of claim 1, wherein said detecting of steps b), c) and d) is carried out at a wavelength between 380 nm and 780 nm, at a wavelength between 470 and 550 nm, or at a wavelength of 505 nm.

3. The method of claim 1, wherein said biological sample is saliva, serum, plasma, whole blood, urine, tears, or sweat.

4. The method of claim 1, wherein Reagent 2 suitable for detecting AC in the biological sample further comprises an inorganic zirconium salt.

5. The method of claim 4, wherein said inorganic zirconium salt is selected from the group consisting of fluoride, chloride, bromide, iodide, and mixtures thereof, and said ferric salt is selected from the group consisting of fluoride, chloride, bromide, iodide, carbonate, sulfate, nitrate, and mixtures thereof.

6. The method of claim 1, wherein detecting total cholesterol comprises:
   providing a first and a second biological sample, wherein said first biological sample was obtained at a time prior to the second biological sample;
   detecting TC in the first biological sample to obtain a baseline level of TC ($TC_b$);
   detecting TC in the second biological sample to obtain a present level of TC ($TC_x$);
   wherein said oxidative balance is determined using formula [a]

OBRI=OI×K1/PI×ΔTC  [a], where K1 is a constant equal to 9.1 in a human being and equal to 5.95 in a rat, and ΔTC is the ratio $TC_x/TC_b$.

* * * * *